United States Patent [19]

Weinshenker

[11] 3,975,334

[45] Aug. 17, 1976

[54] POLYMERIC ORGANOTIN HYDRIDE REAGENTS

[75] Inventor: Ned M. Weinshenker, Palo Alto, Calif.

[73] Assignee: Dynapol, Palo Alto, Calif.

[22] Filed: May 8, 1974

[21] Appl. No.: 467,951

[52] U.S. Cl. ............................... 526/19; 260/2.5 R; 260/2.5 H; 260/343.2 R; 260/586 P; 260/599; 260/601 R; 260/635 A; 260/650 R; 526/47

[51] Int. Cl.² ..................... C08F 13/00; C08F 27/04

[58] Field of Search ......... 260/80 L, 88.1 P, 94.6 R, 260/93.5 R, 93.5 S, 93.5 A, 2.5 R, 2.5 H, 85.1

[56] References Cited
UNITED STATES PATENTS

| | | | |
|---|---|---|---|
| 2,253,128 | 8/1941 | Langkammerer | 260/80 L |
| 3,450,797 | 6/1969 | Schafer | 260/888 |

*Primary Examiner*—Christopher A. Henderson, Jr.
*Attorney, Agent, or Firm*—William H. Benz

[57] ABSTRACT

Insoluble polymeric organotin hydrides of the formula:

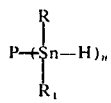

wherein P represents an organic polymer backbone; R and $R_1$ each represent a hydrogen atom, a lower alkyl group of 1 to 5 carbon atoms, an aryl group of 6 to 10 carbon atoms, or an alkaryl or aralkyl group of from 7 to 10 carbon atoms; and n is a positive number greater than 1 are disclosed. Such polymeric organotin hydrides are useful as reagents for reducing organic compounds such as organic halides, ketones, and aldehydes without the different problem of removing dissolved or dispersed tin impurities from the reduced compounds.

9 Claims, No Drawings

POLYMERIC ORGANOTIN HYDRIDE REAGENTS

BACKGROUND OF THE INVENTION

1. Field of the Invention

The invention relates to polymeric organotin hydrides useful as reducing agents and also to a process for reducing organic compounds using such polymeric organotin hydrides.

2. Description of the Prior Art

Polymers containing tin or other metals in their molecule are known. See, for example, U.S. Pat. Nos. 3,223,686; 3,190,901; and 3,684,752. However, no prior art is known which discloses organic polymers containing organotin hydride functions pendant from main polymer chains. The above-noted U.S. Pat. No. 3,223,686 of Natta et al discloses alkyl tin-containing vinyl monomers [e.g., 5-(trimethylstannyl)pentene-1] which are polymerizable with a transition metal catalyst to high molecular weight, linear, regular non-hydride polymers. The resulting polymer products are disclosed as useful as structural polymers in applications requiring high melting point, high temperature stability, and relatively low flammability.

The use of metal hydrides generally for reducing, e.g., carbonyl compounds to corresponding carbinols, is known. Tin hydrides are among the metal hydrides known to have reducing activity. They are especially attractive in certain applications since they selectively reduce organohalides to hydrocarbons in the presence of ketones, amides, nitriles, etc., which are reduced substantially more slowly. However, a disadvantage of tin hydrides used heretofore is that the tin hydrides are soluble in many desirable organic reaction media and thus it is sometimes difficult to remove them from the reduced compound, thereby lowering the efficiency of the method.

There is a need, therefore, for reducing compounds, especially tin hydride compounds, which are both effective in reduction reactions and easy to separate from reaction mixtures after use.

SUMMARY OF THE INVENTION

It is a primary object of the present invention to provide organotin hydride compounds useful as reducing agents, particularly in the reduction of carbonyl compounds to the corresponding carbinols and in the reduction of organohalides to hydrocarbons.

It is a further object of the invention to provide organotin hydride compounds which are effective as reducing agents without the drawbacks of related compounds of the prior art.

It is yet a further object of the invention to provide a process for reducing organic compounds using such organotin hydrides.

It is yet another object of the invention to provide a process for reducing aldehydes and ketones to the corresponding carbinols using such organotin hydrides.

It is another object of the invention to provide a process for reducing alkyl and aryl halides to the corresponding hydrocarbons and for reducing acid halides to the corresponding aldehydes, using such organotin hydrides.

Other objects and advantages will become apparent from the ensuing descriptions.

The above objects may be realized with the polymeric organotin hydride of the present invention as represented by the formula:

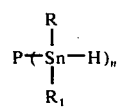

wherein P is an organic polymer backbone or chain, preferably a cross-linked polymer so as to be insoluble in organic reduction media; R and $R_1$ each represent a hydrogen atom, a $C_1$-$C_5$ lower alkyl group, a $C_6$-$C_{10}$ aryl group, a $C_7$-$C_{10}$ aralkyl group, or a $C_7$-$C_{10}$ alkaryl group; and n is a number having a positive value greater than 1.

The invention also includes a process for reducing organic compounds comprising contacting the organic compounds in liquid phase with the above solid polymeric organotin hydride and then liberating, separating, and recovering the reduced organic compounds.

DESCRIPTION OF THE PREFERRED EMBODIMENTS

Broadly stated and as depicted in formula (I), the polymeric organotin hydrides of this invention comprise an organic polymer backbone [P in formula (I)] having a plurality (n) of organotin hydride groups

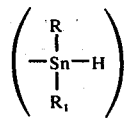

pendant therefrom.

The polymer backbone is an organic polymer selected from polymers which offer active carbons which can bond directly to tin molecules in a C-Sn covalent bond. The polymer backbone should be substantially insoluble in organic reaction media such as hydrocarbons, ethers, alcohols, and the like. This insolubility is required if the advantageous easy separation and recovery of the tin reagent is to be realized. Suitably, the reagent is not soluble to an extent of more than about 0.1% w (basis reaction medium). This insolubility may be achieved by using as P long polymer chains having at least 30 carbons and preferably at least 50 carbons. Preferably it is achieved by employing as P a polymer cross-linked to an extent that it merely swells when placed in organic solvents, rather than dissolving in the solvents. Generally, P is a hydrocarbon, including saturated aliphatic hydrocarbons and aromatically unsaturated hydrocarbons, although if desired, hetero atoms such as oxygen, nitrogen, and sulfur may be included so long as they are in a configuration which does not undergo reduction or other reaction with tin hydrides.

P thus may be a wide range of structures such as are exemplified by

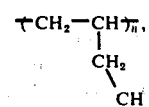

wherein n is 10 or greater, (which results when 1,2-polybutadiene is the starting material for P);

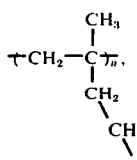

wherein n is 10 or greater (which results when 1,2-polyisoprene is the starting material for P);

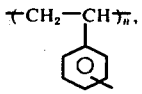

wherein n is 7 or greater, (which results when polystyrene is the starting material for P); and

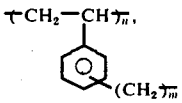

wherein n is 7 or greater and m is from 1 to 5, (which results when poly(lower alkyl styrene) such as poly(methyl, ethyl, or butyl styrene) is used as the starting material for P).

These materials are merely exemplary and may be replaced by other materials meeting the polymer's requirements without departing from this invention.

As noted, preferably the P polymer is cross-linked. Suitably, P contains from about 0.001 to about 0.1 cross-links for each carbon atom in P. These cross-links may be introduced free-radically or by use of coagents such as dienes (for example, divinylbenzene or 1,4-butadiene), or by other methods known in the art. When P is cross-linked, it is generally not possible to accurately place a value on n, since an entire particle of polymer may be one linked together molecule, giving n a meaninglessly high value. In such a case, as well as in the non-cross-linked case (where n is a relatively low number) it is possible to define the polymer structure in terms of moles of tin per gram of overall polymeric reagent. By this method, the theoretical maximum amount of tin is about 6 millimoles/gram, which amount corresponds to a maximum substitution of trihydric tin on a 4 carbon unit repeating polymer. In a reagent having polystyrene as P, the maximum possible tin is 4.4 millimoles/gram of reagent. Suitably, the reagents contain from about 0.1 millimoles or tin/gram up to the theoretical maximum which, as noted, is somewhere between about 4 and 6 millimoles/gram, depending on the exact nature of P. Preferably, the reagents contain from 0.5 to 4–6 millimoles of tin per gram of reagent.

Another desirable characteristic of polymer P is porosity. When P is porous, it enables the reaction media to better contact the reagent's tin hydrides and permits tin loadings closer to theoretical maximum. Preferably, P has a porosity of at least 10%, such as from 10% to 60%; most preferably with pores of a macroporous size, that is, that range in size from 200A to 2000A. For ease of use, P should be in a particulate form.

The presently preferred polymer P is macroporous, solid particulate polystyrene cross-linked with from 0.1 to 10% by weight of divinylbenzene (which amount is equivalent to from about 0.001 to about 0.1 cross-link bonds for each carbon atom in the polystyrene matrix. The particles of this polystyrene are from about 0.5 mm in diameter up to about 1 cm in diameter.

The tin hydrides of this invention as depicted in formula (I) include monohydrides, dihydrides, and trihydrides, with the dihydrides being preferred because of their relatively superior stability and activity (i.e., reducing power). Thus, R and $R_1$ in formula (I) may each be the same or different and are selected from the group consisting of a hydrogen atom, a lower alkyl group having from 1 to 5 carbon atoms (methyl, ethyl, the propyls, the butyls and the amyls), an aryl group having from 6 to 10 carbon atoms (phenyl or naphthyl), an aralkyl group having from 7 to 10 carbon atoms (e.g., benzyl, phenylethyl, phenylbutyl, etc.), or an alkaryl group having from 7 to 10 carbon atoms (e.g., methylphenyl, ethylphenyl, butylphenyl, dimethylphenyl, etc.). While it is the intention to include within the scope of R and $R_1$ all of the groups within the above broad designations, lower alkyl groups of from 1 to 4 carbon atoms are preferred R and $R_1$ groups.

Specific examples of operable polymers are:

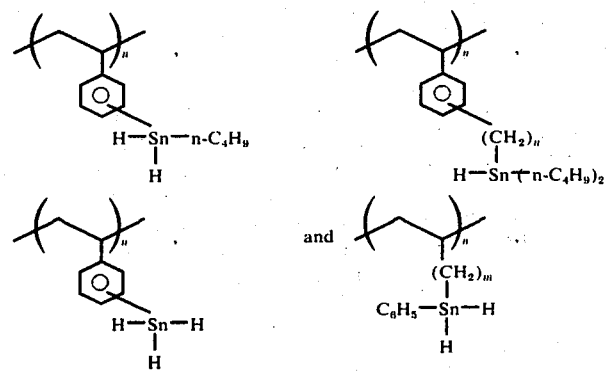

wherein n is as defined and m has a value from 1 to 5.

The polymeric organotin hydrides of the invention may be prepared by attaching the tin hydride function to the polymer chain by any suitable method. For example, it is known that a Grignard reagent will react with an alkyltin halide to provide a different alkyltin halide according to the equation:

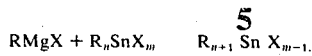
   1.

Therefore, by analogy, polymeric organotin hydrides may be prepared by the following technique (using polystyrene as an example of the polymer, where P indicates the methylenemethine polymer chain or its precursor:

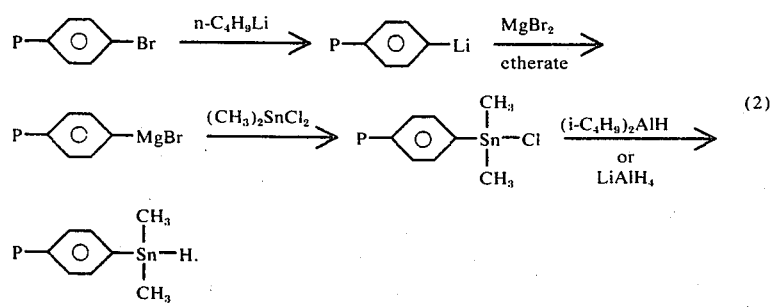

An alternative route for the preparation of polymeric tin hydride reagents starts with cross-linked poly-1,2-butadiene and is shown in scheme (3):

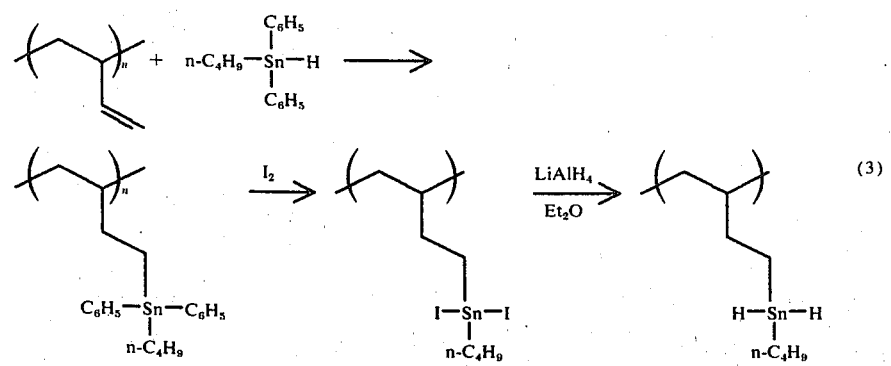

A further alternative is similar to those of reaction schemes (2) and (3) and comprises using either the brominated polystyrene or the chloromethylated polystyrene and n-butyltin trichloride to obtain the polymeric tin hydride (III):

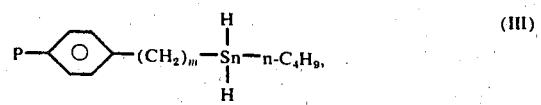

where m is 0 or 1 depending on the starting material.

Regardless of the method employed to make the polymeric organotin hydrides, its structure is controlled by the particular starting material and organotin compound employed. The reactions are generally performed in inert solvents such as benzene, ether, etc., using reactants which are either commercially available or which can be easily synthesized.

The main polymer chain may be cross-linked prior to preparing the polymeric organotin hydrides of the invention, or hydrides may be formed and then polymerized and cross-linked. The technique employed and the degree of cross-linking obtained are not critical, and those skilled in the art are aware of conventional processes for accomplishing the desired results.

As pointed out above, the compounds of the invention find particular utility as reducing agents for carbonyl compounds, such as aldehydes and ketones. Carbinols are produced directly from this reaction and there are no significant tin impurities to be removed from the carbinol product. In addition, the polymeric organotin hydrides of the invention are also useful in reducing alkyl and aryl halides to the corresponding hydrocarbons and in reducing acid halides to the corresponding aldehydes.

These reduction reactions are performed under the following general conditions. It will be appreciated that these are merely a guide and that variations may be made — still remaining within the scope of this invention. The compound to be reduced is contacted as a liquid with the solid polymeric organotin hydride, generally at a moderately elevated temperature, for a period of time necessary to perfom the reduction, said time generally ranging from 1 to 40 hours. The temperature may vary from about room temperature (20°) to 150°C, preferably it is in the range of from 65° to 110°C. The reduction is conveniently carried out at atmospheric pressure, although a super-atmospheric pressure of up to 10 atmospheres may be employed, if desired. The reaction is effected in liquid phase. This liquid phase may be provided by the compound being reduced, or may be provided by an added inert reaction solvent; that is, a solvent which does not undergo reduction or other reaction with the tin reagent under the reduction conditions. Typical solvents include: hydrocarbons, both saturated and aromatically unsaturated, such as cyclohexane and benzene; ethers, such as THF, and the like, with aromatic hydrocarbons being preferred.

In the case of alkyl or aryl halides or acid halides, the conversion to the corresponding hydrocarbon or aldehyde is effected directly in one step; for example, when benzylchloride is contacted with the reagents of this invention it is converted directly to toluene, the chlorine atom being replaced by a hydride hydrogen.

In the case of carbonyl reduction, a second step — a hydrolysis step — is required to complete the reduction. When the carbonyl is contacted with the reagent, the C=O group assimilates a single hydrogen from the reagent and also becomes associated with the tin atom. When this partially reduced material is contacted with dilute acid, such as dilute hydrochloric acid or the like, it takes up a hydrogen from the acid, and the reduction is completed.

The amount of tin reagent employed should be enough to provide adequate hydrogen for reduction, that is, at least one equivalent of hydrogen for each equivalent of reduction desired, and preferably a slight excess (i.e., 1.1 to 2.0 equivalents of hydrogen for each equivalent of reduction). Thus, with the trihydride reagents, one mole will provide three equivalents of hydrogen and effect three equivalents of reduction. The dihydrides provide two equivalents of hydrogen per mole, etc.

After the reduction and, if applicable, hydrolysis is complete, the polymeric reagent, since it is insoluble, is easily separated from the reaction medium and reaction products and recovered by filtration, centrifugation, decantation, and/or settling. The recovered reagent may be washed and regenerated in accord with the general preparative scheme and reduced. The reduced compound which is separated may be isolated from the reaction medium and purified, if desired, by the art-known techniques of distillation, evaporation, and the like. It should be reemphasized that the reduction reagent removal is rendered extremely easy by its particulate polymeric nature.

The present invention will be further illustrated by reference to the following Examples, which are intended to be merely illustrative and not limiting in nature. Unless otherwise indicated, all "parts" and "percentages" are by weight.

EXAMPLE I

50 Grams of Amberlite XE-305 (a cross-linked polystyrene resin available from Rohm and Haas Co.) is suspended/dissolved in 350 ml of carbon tetrachloride solvent. 100 Grams of Tl(OCOCH$_3$)$_3$ 1.5 H$_2$O catalyst is added and 18 ml of bromine as gas is then bubbled into the reaction mixture while maintaining a temperature of 5°C for a period of 1 hour. Then the mixture is refluxed for 2 hours, during which time it changes from brown to yellow. It is cooled to yield 78 g of brominated resin. This resin is analyzed and found to have the following analysis:

```
58.11%  -  Carbon
 4.78%  -  Hydrogen
32.14%  -  Bromine.
```

Thus, bromine is incorporated in the resin in an amount of 4.02 meg/g or resin.

67 Grams of the brominated resin is dissolved/suspended in 450 g of tetrahydrofuran (THF) and 350 meg of n-butyllithium is added thereto. The reaction is conducted at −55°C for a period of 1 hour, after which time the temperature is raised to 0°C and 250 ml of MgBr etherate (0.4 moles) is added thereto. This temperature is maintained for 2 hours, after which time 130 g of n-butyltin trichloride is added thereto. The temperature is maintained at 25°C for 16 hours, and 57.5 g of product is recovered, represented by the formula

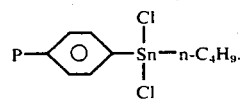

The results of an elemental analysis are as follows:

```
62.47%  -  Carbon
 5.98%  -  Hydrogen
 8.90%  -  Tin
 6.85%  -  Chlorine
 0.00%  -  Bromine.
```

The MgBr etherate is prepared by the House method; i.e., by reacting, at reflux temperature, 75.2 g of 1,2-dibromoethane with 9.8 g of magnesium in a 2:1 mixture of ether/benzene.

77 Grams of the dichlorobutyltin compound (IV) is dissolved/suspended in 400 ml of benzene of THF at −55°C, and 200 ml of 25% diisobutylaluminum hydride or 200 ml of 0.9 M lithium aluminum hydride/THF solution added thereto. After 5 hours at room temperature, 63 g of the dihydride,

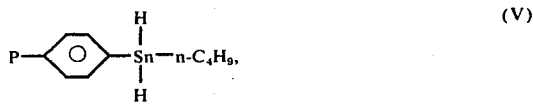

is recovered. The results of an elemental analysis are as follows:

```
74.29%  -  Carbon
 6.63%  -  Hydrogen
 8.91%  -  Tin
 0.00%  -  Aluminum
 0.00%  -  Chlorine.
```

EXAMPLE II 0.174 Grams of 4-phenylcyclohexanone is dissolved/suspended in 40 ml of THF and 2.5 g of the dihydride (V) prepared above is then added thereto. The reaction is performed using the temperatures and times indicated in Table I below. The product of reaction, after separating the polymer and removing the solvent, which comprises a mixture of the ketone starting material and 4-phenylcyclohexanol, is subjected to hydrolysis to complete the reduction. The reaction is repeated using toluene as solvent and somewhat higher temperatures, as shown in Table I. The yield of the carbinol in both runs is determined both before and after the hydrolysis, and the results are also shown in Table I.

TABLE I

| Reaction Time (Hrs.) | Reaction Temp. (C°) | Before Hydrolysis | After Hydrolysis | Total Yield |
|---|---|---|---|---|
| 17 | room temp. | 0.10% | 8% | 8.1% |
| 16 | 65 | 17% | 18% | 35% |
| 4* | 111 | — | 47% | 47% |
| 44** | 111 | — | 61% | 61% |

*Toluene employed as solvent instead of THF.

The unsaturated compounds which can be reduced with the polymeric organotin hydride of the invention include, aldehydes, ketones, alkyl halides, aryl halides, and acid halides.

The following are examples of specific compounds falling within the above broad classifications which can be reduced according to the invention:

A. aldehydes benzaldehyde, octanal, acetaldehyde, cyclopentanecarboxaldehyde

B. ketones 4-phenylcyclohexanone, methyl t-butylketone, $\Delta^4$-cholestenone, progesterone, benzophenone C. alkyl halides octyl iodide, PG iodide,

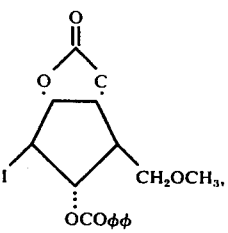

benzyl chloride,
benzyl iodide.

D. aryl halides phenyliodide

E. acid halides benzoyl chloride.

While the invention has been shown and described by reference to preferred embodiments thereof, it is to be understood that various changes, modifications, and/or substitutions may be made therein without departing from the spirit and scope of the invention, which is as defined by the appended claims.

What is claimed is:

1. A solid polymeric organotin hydride compound of the formula

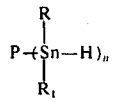

wherein P represents a porous crosslinked substantially organic solvent insoluble hydrocarbon polymer; R and $R_1$ each represent hydrogen, a lower alkyl group having from 1 to 5 carbon atoms, an aryl group having from 6 to 10 carbon atoms, or an aralkyl or alkaryl group having from 7 to 10 carbon atoms; and n is a positive value greater than 1.

2. The compound of claim 1, wherein one only of said R and $R_1$ is hydrogen and the other of said R and $R_1$ is said lower alkyl, aryl, aralkyl, or alkaryl group.

3. The compound of claim 1, wherein both of said R and $R_1$ are said lower alkyl, aryl, aralkyl, or alkaryl group.

4. A solid polymeric organotin hydride compound of the formula

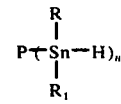

wherein P represents a porous crosslinked polystyrene hydrocarbon polymer; R and $R_1$ each represent hydrogen, a lower alkyl having from 1 to 5 carbon atoms, an aryl group having from 6 to 10 carbon atoms, or an aralkyl or alkaryl group having from 7 to 10 carbon atoms; and n is a positive number having a value greater than 1.

5. The compound of claim 4, wherein said crosslinked polystyrene is macroporous.

6. The compound of claim 5, wherein only one of said R and $R_1$ is hydrogen and the other of said R and $R_1$ is a lower alkyl group.

7. The compound of claim 4, wherein said polymer contains from 0.1 to 0.001 cross-linking groups for each carbon in said polymer.

8. The compound of claim 4, wherein one only of said R and $R_1$ is hydrogen and the other of said R and $R_1$ is said lower alkyl, aryl, aralkyl, or alkaryl group.

9. The compound of claim 4, wherein both of said R and $R_1$ are said lower alkyl, aryl, aralkyl, or alkaryl group.

* * * * *